US008518109B2

(12) United States Patent
Shea et al.

(10) Patent No.: US 8,518,109 B2
(45) Date of Patent: Aug. 27, 2013

(54) OPTICAL COUPLING GEL FOR EYE IMAGING

(75) Inventors: William Shea, Pleasanton, CA (US);
Barry Linder, Danville, CA (US);
Phillip Baker, Walnut Grove, CA (US);
Yan Zhou, Pleasanton, CA (US)

(73) Assignee: Clarity Medical Systems, Inc., Pleasanton, CA (US)

( * ) Notice: Subject to any disclaimer, the term of this patent is extended or adjusted under 35 U.S.C. 154(b) by 49 days.

(21) Appl. No.: 12/606,017

(22) Filed: Oct. 26, 2009

(65) Prior Publication Data

US 2010/0121442 A1 May 13, 2010

Related U.S. Application Data

(60) Provisional application No. 61/111,945, filed on Nov. 6, 2008.

(51) Int. Cl.
*A61F 2/16* (2006.01)
*A61F 2/14* (2006.01)

(52) U.S. Cl.
USPC .......................................... 623/6.11; 623/4.1

(58) Field of Classification Search
USPC .................. 424/78.04, 80, 81, 329, 344, 427; 514/912–915, 954; 623/4.1, 6.11
See application file for complete search history.

(56) References Cited

U.S. PATENT DOCUMENTS

| 4,029,817 | A | * | 6/1977 | Blanco et al. | 514/496 |
| 4,819,617 | A | * | 4/1989 | Goldberg et al. | 128/897 |
| 2008/0020044 | A1 | * | 1/2008 | Alam et al. | 424/486 |

OTHER PUBLICATIONS

Jay W. McLaren et al. Measuring Corneal Thickness with the ConfoScan 4 and Z-Ring Adapter, Eye & Contact Lens 33(4), 185-190, 2007.*
Pascal Furrer et al, Confocal Microscopy as a Tool for the Investigation of the Anterior part of the Eye, Journal of Ocular Pahramacology and therapeutics, vol. 13(6), 559-578, 1997.*

* cited by examiner

*Primary Examiner* — Michael G Hartley
*Assistant Examiner* — Jagadishwar Samala
(74) *Attorney, Agent, or Firm* — Kilpatrick Townsend & Stockton LLP

(57) ABSTRACT

The invention discloses an optical coupling gel that has a set of desired features for application in eye imaging, including being approved for eye contact, optically transparent, able to maintain normal hydration of the ocular surface, flexible and capable of maintaining a distinct shape, minimal in breakdown/change during use, and easily dispensable/applicable. In one embodiment, the gel is made of Sodium Carboxy Methylcellulose (SCMC), where the amount of the cellulose determines the viscosity of the gel for its particular application. The right amount of gel is contained in an applicator for application to one or two eyes.

4 Claims, 1 Drawing Sheet

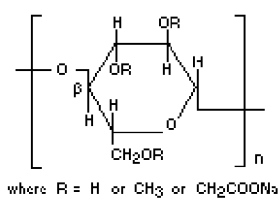
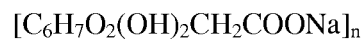
Diagram A, the structural and chemical formula of one example of the disclosed optical coupling gel, Sodium Carboxy Methylcellulose (SCMC).

OPTICAL COUPLING GEL FOR EYE IMAGING

RELATED APPLICATIONS

This application claims priority from a provisional application entitled OPTICAL COUPLING GEL FOR EYE IMAGING, Application No. 61/111,945, filed Nov. 6, 2008, which is hereby incorporated by reference for all purposes.

TECHNICAL FIELD

The present disclosure relates generally to optical coupling gels for use with an eye examination and imaging device.

BRIEF DESCRIPTION OF THE DRAWINGS

Diagram A illustrates the structural and chemical formula of one example of the disclosed optical coupling gel, Sodium Carboxy Methylcellulose (SCMC).

DESCRIPTION OF EXAMPLE EMBODIMENTS

Overview

This invention is a customized optical coupling gel that results in optimal visualization/clarity when used for imaging of the anterior chamber or posterior segment of the eye while at the same time providing the appropriate hydration/lubrication to the patient's eye during the entire imaging session.

Description

Reference will now be made in detail to various embodiments of the invention. Examples of these embodiments are illustrated in the accompanying drawings. While the invention will be described in conjunction with these embodiments, it will be understood that it is not intended to limit the invention to any embodiment. On the contrary, it is intended to cover alternatives, modifications, and equivalents as may be included within the spirit and scope of the invention as defined by the appended claims. In the following description, numerous specific details are set forth in order to provide a thorough understanding of the various embodiments. However, the present invention may be practiced without some or all of these specific details. In other instances, well known process operations have not been described in detail in order not to unnecessarily obscure the present invention. Further, each appearance of the phrase an "example embodiment" at various places in the specification does not necessarily refer to the same example embodiment.

There are other eye-lubricating gels that are used currently for dry eyes or for the ease of surgical operation on an eye. However, none of these gels are formulated and optimized to act as an optical coupling gel for the imaging of both the anterior chamber and the posterior segment of the eye. When an eye is imaged by an eye imaging device that needs to have a good optical light path connection with the eye through an optically transparent coupling gel, a key issue associated with using the existing gels as the optical coupling gel is that since they are designed for other applications, they do not have the desired viscosity and hence would automatically shape itself based on its optical and mechanical properties due to surface tension and gravity or drip off from the eye especially if the patient is sitting upright.

This invention is an improvement to existing eye gel products such as GenTeal and GoNak, which are not optimized for optical coupling with desired viscosity, but mainly used for dealing with dry eyes and other eye ailments.

This invention is a compound made of existing materials (cellulose, de-ionized water, polyvinyl alcohol, hydrogels or silicone, for examples), that result in the following properties; approved for eye contact, optically transparent, maintenance of normal hydration of the ocular surface, flexibility and capability to maintain a distinct shape, minimal breakdown/change during use, and easily dispensed/applied. The presently invented gel works by providing an optical bridge from the optical front surface of a camera (fundus or slit lamp camera, for example) to the eye (the anterior of an eye, for example), thus providing a means to acquire a good image of the eye without the need for a good contact of the camera optical element with the eye. Meanwhile, this invention also enables one to maintain or adjust the object distance while the optical light path connection is optimized between the camera lens and the object being imaged because optical reflections caused by optical interfaces of relatively large refractive index differences can be substantially reduced, while providing a mechanism for optimizing focus.

The material in its original form is a cellulose based product of varying percent when combined with water. In an example embodiment the compound Sodium Carboxymethyl Cellulose (CMC) is utilized. Diagram A illustrates the key composition of the optical coupling gel. The cellulose percentage of the mixture determines the viscosity and also the particular application for its use/customization.

Tests utilizing 4, 5, and 6 percentages of cellulose, denominated Gel type A, B, and C respectively, have been conducted. The results of comparative transmission measurements performed on Gel types A, B, and C and other products are presented in Appendix A attached to the end of this description.

The invented gel provides a more efficient and effective way to acquire images of the anterior and posterior of the eye. It accomplishes this by providing an optically clear medium between the camera lens and eye that will maintain its shape and viscosity during the entire imaging process. These features reduce the number of re-applications of the gel during an imaging session, reduce the debris from repeated applications, allow imaging to be performed in a prone or upright position, enable better imaging opportunities due to the larger amount of gel used for coupling.

For anterior chamber imaging, in real practice, the gel gap distance between the lens of the instrument and the eye can vary from tens of microns to 7 mm Measurements of relative difference in light transmission with respect to GenTeal Gel were made of Gels having concentrations of sodium carboxy methylcellulose (SCMC) of between about 4% and 6% in distilled water.

It should also be noted that Type A Cellulose Gel has some air bubbles when sandwiched, while type C has less air bubbles. Both type B Cellulose Gel and GenTeal Gel have no air bubbles when sandwiched. So type B is the best in both light transmission and air-bubble-freeness. For the 7mm gel thickness case, Gel Y is the best, Gel X is the second best, followed by Gel Z. The reduction in transmittance when compared to GenTeal is about 8% to 15% on average, the blue light spectrum side has more reduction in transmission which for the Gel Z case is 20%.

In addition to the gel composition aspect of the invention, the applicator is also part of the invention. The applicator can be customized for a particular use/application. For example, in ROP imaging a single applicator can be designed to deliver the right amount of gel for the eye; the applicator could be a syringe with enough gel for both eyes and directions on how much to dispense onto each eye for imaging. This supports the claims of efficient and cost-effective invention.

The key factors of the gel include optimized optical coupling, "lubrication" of patient's eye, minimal mess, less product waste, cost effectiveness, customized applicators for procedure.

The important factors of this invention are optical clarity and viscosity. The gel can consist of any material(s) that meets the aforementioned key factors, for example polyvinyl alcohol. If the gel is to be used for human use then it must be biocompatible. The gel could also be silicone or rubber based or another compound. In addition, the material needs to be capable of undergoing a sterilization procedure while maintaining its aforementioned features of clarity and viscosity.

The gel or other material could be formed into a shape that provides enough durability to hold a defined shape long enough for its application. For example, the gel's viscosity could be high enough to be formed in a mold, packaged then applied to the camera's tip and maintain its shape for a particular use.

The gel could also be adapted to include specific pharmaceutical components such as anesthetics or antibiotics, for example. In addition, the gel could carry a specific dye for use in florescence or better detection/observation of surface anomalies, for example.

In addition to ophthalmic imaging, the presently invented gel can be applied to any imaging that will benefit from the use of a coupling gel. For example, it can used for surgical imaging, wound imaging, ultrasound imaging; high magnification microscopic imaging, as liquid lens interfaces for high numerical aperture optics or close proximity LED arrays.

The invention has now been described with reference to the example embodiments. Alternatives and substitutions will now be apparent to persons of skill in the art. For example, the optical gel could be applied to the eye of the patient instead of to the surface of the instrument. Accordingly, it is not intended to limit the invention except as provided by the appended claims.

What is claimed is:

1. A method comprising:
dispensing an optically transmissive gel, having a maintainable shape that conforms to the surface of a lens being part of an ophthalmic examination instrument, to the surface of the lens without the formation of significant air bubbles that would decrease the transmission of light through the optically transmissive gel, with the optically transmissive gel having a concentration of sodium carboxy methylcellulose (SCMC) of between about 4% and 6% in distilled water;
positioning the lens close enough to the surface of an eye under examination so that the optically transmissive gel bridges the gap between the lens and the surface of the eye under examination; and
adjusting the object distance between the lens and the surface of the eye within the range of from about 1 mm to about 7 mm while performing anterior chamber angle imaging of the eye under examination and optical coupling is maintained between the lens and the surface of the eye under examination by the optically transmissive gel to facilitate acquiring good images of the anterior chamber of the eye under examination;
where the viscosity level of the optically transmissive gel allows the optically transmissive gel to be dispensed without formation of significant light-scattering air bubbles and to remain on the lens during positioning, to maintain a defined shape with minimal breakdown or change during use and to be easily removed from the surface of the eye after use.

2. The method of claim 1 where the optically transmissive gel includes specific pharmaceutical components such as anesthetics, antibiotics or fluorescent dyes.

3. The method of claim 1 further comprising:
dispensing the gel with an applicator.

4. The method of claim 1 where the transmissive gel is formed in a mold, packaged and applied to the lens with its shape maintained for a particular use.

* * * * *